US008231525B2

(12) United States Patent
Cohen et al.

(10) Patent No.: US 8,231,525 B2
(45) Date of Patent: Jul. 31, 2012

(54) ENDOSCOPE CHANNEL CAP

(75) Inventors: Adam L. Cohen, Arlington, MA (US); John Golden, Norton, MA (US); Liem T. Vu, Needham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1109 days.

(21) Appl. No.: 11/320,491

(22) Filed: Dec. 29, 2005

(65) Prior Publication Data
US 2006/0135850 A1 Jun. 22, 2006

Related U.S. Application Data

(63) Continuation of application No. 10/765,842, filed on Jan. 29, 2004, now Pat. No. 7,025,721.

(51) Int. Cl.
*A61M 5/178* (2006.01)
*A61B 1/00* (2006.01)
*A61B 1/12* (2006.01)

(52) U.S. Cl. .............. 600/154; 600/159; 604/167.01; 604/167.06

(58) Field of Classification Search .......... 600/104, 600/121, 129, 127, 131, 123, 153–159; 604/607.01–607.06
See application file for complete search history.

(56) References Cited

U.S. PATENT DOCUMENTS

| 4,198,958 A | 4/1980 | Utsugi |
| 4,367,905 A | 1/1983 | Nauta |
| 4,649,904 A * | 3/1987 | Krauter et al. ............... 600/154 |
| 4,653,477 A | 3/1987 | Akui et al. |
| 4,715,360 A | 12/1987 | Akui et al. |
| 4,794,913 A | 1/1989 | Shimonaka et al. |
| 4,809,679 A | 3/1989 | Shimonaka |
| 4,886,177 A | 12/1989 | Foster |
| 4,909,798 A | 3/1990 | Fleischhacker et al. |
| 4,920,953 A | 5/1990 | McGown |
| 4,969,565 A | 11/1990 | Justal et al. |
| 5,000,533 A | 3/1991 | Gerwers |
| 5,098,064 A | 3/1992 | Daly et al. |
| 5,104,379 A | 4/1992 | Nakamura et al. |
| 5,106,054 A | 4/1992 | Mollenauer et al. |
| 5,114,408 A | 5/1992 | Fleischhaker et al. |
| 5,127,626 A | 7/1992 | Hilal et al. |

(Continued)

FOREIGN PATENT DOCUMENTS
DE      199 11 911 A1      9/1999
(Continued)

OTHER PUBLICATIONS

International Search Report and Written Opinion for PCT/US2005/00028 dated Apr. 29, 2005.

*Primary Examiner* — Matthew J Kasztejna
*Assistant Examiner* — Ryan Henderson
(74) *Attorney, Agent, or Firm* — Seager, Tufte & Wickhem, LLCb

(57) ABSTRACT

The invention relates to an endoscope channel cap that may be used separately with two or more endoscopes each having a cap interface portion with a different configuration. The channel cap also may include one or more seals to maintain insufflation pressure both when an endoscopic instrument is inserted in a working channel of the endoscope and when the instrument is not inserted in the channel.

8 Claims, 5 Drawing Sheets

U.S. PATENT DOCUMENTS

| | | | |
|---|---|---|---|
| 5,147,305 A | 9/1992 | Nakamura et al. |
| 5,167,636 A | 12/1992 | Clement |
| 5,199,948 A | 4/1993 | McPhee |
| 5,211,633 A | 5/1993 | Stouder, Jr. |
| 5,242,389 A | 9/1993 | Schrader et al. |
| 5,300,033 A | 4/1994 | Miller |
| 5,304,143 A | 4/1994 | Green et al. |
| 5,312,362 A | 5/1994 | Pfolsgraf et al. |
| 5,320,602 A | 6/1994 | Karpiel |
| 5,338,307 A | 8/1994 | Stephens et al. |
| 5,338,313 A | 8/1994 | Mollenauer et al. |
| 5,350,362 A | 9/1994 | Stouder, Jr. |
| 5,350,363 A | 9/1994 | Goode et al. |
| 5,354,280 A | 10/1994 | Haber et al. |
| 5,357,978 A | 10/1994 | Turk |
| 5,385,552 A | 1/1995 | Haber et al. |
| 5,391,153 A | 2/1995 | Haber et al. |
| 5,395,342 A | 3/1995 | Yoon |
| 5,397,302 A | 3/1995 | Weaver et al. |
| 5,397,335 A | 3/1995 | Gresl et al. |
| 5,407,433 A | 4/1995 | Loomas |
| 5,423,762 A | 6/1995 | Hillstead |
| 5,429,619 A | 7/1995 | Furnish |
| 5,431,150 A | 7/1995 | Yabe et al. |
| 5,441,486 A | 8/1995 | Yoon |
| 5,456,284 A | 10/1995 | Ryan et al. |
| 5,478,318 A | 12/1995 | Yoon |
| 5,512,053 A | 4/1996 | Pearson et al. |
| 5,514,098 A | 5/1996 | Pfoslgraf et al. |
| 5,549,594 A | 8/1996 | Brunken |
| 5,562,632 A | 10/1996 | Davila et al. |
| 5,607,397 A | 3/1997 | Stephens et al. |
| 5,613,956 A | 3/1997 | Patterson et al. |
| 5,630,787 A | 5/1997 | Yabe et al. |
| 5,674,181 A | 10/1997 | Iida |
| 5,685,858 A | 11/1997 | Kawand |
| 5,733,243 A | 3/1998 | Yabe et al. |
| 5,738,630 A | 4/1998 | Suzuki et al. |
| 5,820,600 A | 10/1998 | Carlson et al. |
| 5,820,606 A | 10/1998 | Davis et al. |
| 5,823,995 A | 10/1998 | Fitzmaurice et al. |
| 5,860,913 A | 1/1999 | Yamaya et al. |
| 5,863,286 A | 1/1999 | Yabe et al. |
| 5,891,056 A | 4/1999 | Ramzipoor |
| 5,919,004 A | 7/1999 | Christenson |
| 5,921,971 A | 7/1999 | Agro et al. |
| 5,954,957 A * | 9/1999 | Chin-Loy et al. | 210/232 |
| 5,997,515 A | 12/1999 | de la Torre et al. |
| 6,006,002 A | 12/1999 | Motoki et al. |
| 6,053,861 A * | 4/2000 | Grossi | 600/154 |
| RE36,702 E | 5/2000 | Green et al. |
| 6,110,104 A | 8/2000 | Suzuki et al. |
| 6,117,070 A | 9/2000 | Akiba |
| 6,142,981 A | 11/2000 | Heck et al. |
| 6,200,262 B1 | 3/2001 | Ouchi |
| 6,203,533 B1 | 3/2001 | Ouchi |
| D443,929 S | 6/2001 | Wilkinson et al. |
| 6,254,529 B1 | 7/2001 | Ouchi |
| 6,409,220 B1 | 6/2002 | Wing et al. |
| 6,416,499 B2 | 7/2002 | Paul, Jr. |
| 6,554,767 B2 | 4/2003 | Tanaka |
| 6,663,598 B1 | 12/2003 | Carrillo, Jr. |
| 6,689,051 B2 | 2/2004 | Nakada et al. |
| 6,860,869 B2 | 3/2005 | Dennis |
| 6,863,661 B2 | 3/2005 | Carrillo, Jr. et al. |
| 7,025,721 B2 * | 4/2006 | Cohen et al. | 600/154 |
| 2002/0013552 A1 | 1/2002 | Dennis |
| 2003/0181858 A1 | 9/2003 | Lajtai et al. |
| 2003/0208104 A1 | 11/2003 | Carrillo et al. |
| 2004/0049158 A1 | 3/2004 | Ley et al. |
| 2004/0167379 A1 | 8/2004 | Akiba |
| 2005/0165277 A1 * | 7/2005 | Carrillo et al. | 600/154 |

FOREIGN PATENT DOCUMENTS

| | | |
|---|---|---|
| DE | 199 16 866 A1 | 10/1999 |
| DE | 101 52 551 A1 | 7/2003 |
| JP | 02-200234 A | 8/1990 |
| JP | 03-073127 A | 3/1991 |
| JP | 03-111025 A | 5/1991 |
| JP | 3-126428 A | 5/1991 |
| JP | 07-100097 A | 4/1995 |
| JP | 9-094253 A | 4/1997 |
| JP | 09-215658 A | 8/1997 |
| JP | 10-155735 A | 6/1998 |
| JP | 10-165360 A | 6/1998 |
| JP | 10-192227 A | 7/1998 |
| JP | 10-192229 A | 7/1998 |
| JP | 2001-218732 A | 8/2001 |
| JP | 2001-218733 A | 8/2001 |
| JP | 2001-231748 A | 8/2001 |
| JP | 2001-346759 A | 12/2001 |
| JP | 2002-028129 A | 1/2002 |
| JP | 2002-136475 A | 5/2002 |
| JP | 2002-143086 A | 5/2002 |
| JP | 2003-038427 A | 2/2003 |
| JP | 2003-210397 A | 7/2003 |
| JP | 2003-220024 A | 8/2003 |
| JP | 2004-222780 A | 8/2004 |
| JP | 2004-222781 A | 8/2004 |
| JP | 2004-229987 A | 8/2004 |
| JP | 2004-298350 A | 10/2004 |
| JP | 2004-344380 A | 12/2004 |
| JP | 2004-344381 A | 12/2004 |

* cited by examiner

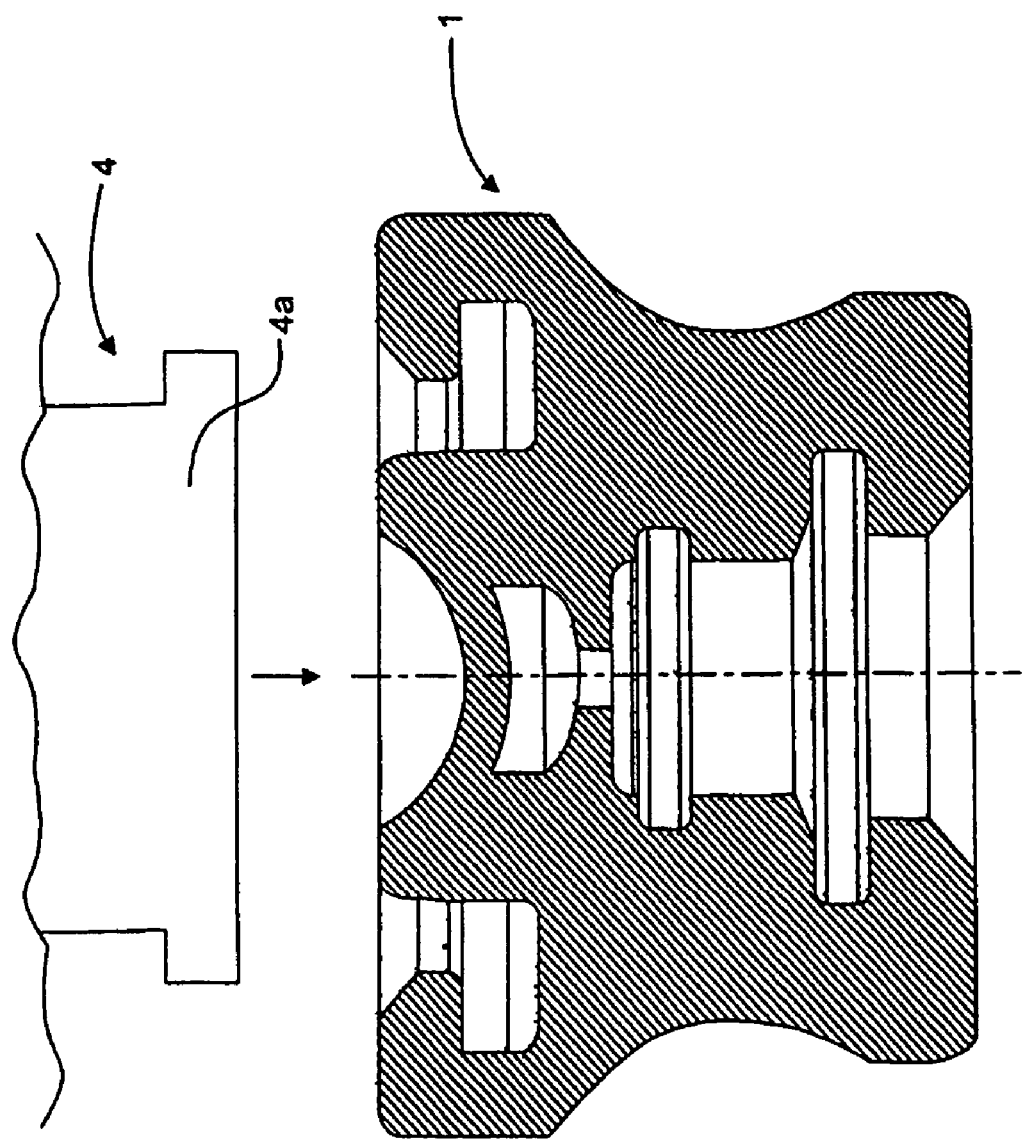

ENDOSCOPE CHANNEL CAP

CROSS-REFERENCE TO RELATED APPLICATIONS

This is a continuation of U.S. patent application Ser. No. 10/765,842, filed Jan. 29, 2004, now U.S. Pat. No. 7,025,721, the entirety of which is incorporated herein by reference.

DESCRIPTION OF THE INVENTION

1. Field of the Invention

The invention relates to an endoscope channel cap that may be used separately with two or more endoscopes each having a cap interface portion with a different configuration.

2. Background of the Invention

Endoscopes may be used to perform a variety of medical procedures. In a typical endoscopic procedure, an endoscope with a working channel is introduced into the body and advanced through a body lumen, for example the gastrointestinal tract. Once the endoscope is positioned in the desired body portion, an endoscopic instrument, for example a biopsy forceps device, is advanced through the working channel of the endoscope to the desired body portion. The endoscopic instrument may then be manipulated as desired.

The endoscopic instrument is advanced through the working channel by first advancing it through an endoscope channel cap which is connected to a cap interface portion at the proximal end of the endoscope. The endoscope channel cap may have a seal portion, through which the endoscopic instrument is advanced, which substantially prevents flow communication across the seal even when the endoscopic instrument is disposed therethrough. For example, the seal may substantially prevent bodily fluids from being ejected from the body via the working channel of the endoscope. In another example, the seal may prevent contaminants from entering the body via the working channel of the endoscope. In a further example, the seal may be configured to maintain an insulation pressure in the desired body portion. Furthermore, different endoscopic instruments may have different configurations that require different seal configurations in order to substantially prevent flow communication across the seal.

Various endoscopes manufactured by different companies, however, have cap interface portions with different configurations. Furthermore, the cap interface portions may have such different configurations that no single endoscope channel cap may accommodate more than one type of cap interface portion. For example, the cap interface portions may include protrusions or other features of widely varying dimensions, shapes, or geometries.

Accordingly, in order to use endoscopes having cap interface portions with different configurations, such as those manufactured by different companies, a different endoscope channel cap must be purchased and used with the corresponding endoscope. For example, endoscopes manufactured by OLYMPUS, PENTAX, and FUJI each have cap interface portions that require a specially configured endoscope channel cap that is incompatible with the other endoscopes. This not only increases costs, as an endoscope channel cap must be purchased for each type of endoscope, but also requires a user to keep track of which cap goes with which endoscope.

Moreover, an endoscopic instrument that inserts through the working channel of the endoscope may require its own specially adapted seal in an endoscope channel cap. This also may increase the cost and complexity of a given endoscopic procedure.

SUMMARY OF THE INVENTION

In accordance with the invention, an embodiment of the invention includes an endoscope channel cap including a first accommodating portion having a first configuration corresponding to an interface of a first endoscope, and a second accommodating portion having a second configuration corresponding to an interface of a second endoscope, the first configuration being different than the second configuration.

In various embodiments, the cap may include any combination of various aspects. For example, the cap may include a third accommodating portion having a third configuration corresponding to an interface of a third endoscope, and the first configuration and the second configuration may be different than the third configuration. In another example, the first and second accommodating portions may be on a first side of the endoscope channel cap and the third accommodating portion may be on a second side of the endoscope channel cap. In a further example, the first accommodating portion may be on a first side of the endoscope channel cap and the second accommodating portion may be on a second side of the endoscope channel cap. In yet another example, the first accommodating portion may be configured to receive the interface of the first endoscope from a first side of the endoscope channel cap, and the second accommodating portion may be configured to receive the interface of the second endoscope from a second side of the endoscope channel cap. In a yet further example, the first accommodating portion may be configured to receive the interface of the first endoscope from aside of the endoscope channel cap, and the second accommodating portion may be configured to receive the interface of the second endoscope from the side of the endoscope channel cap. In still another example, the first and second accommodating portions may open to a same side of the cap. In a still further example, the first and second accommodating portions may be coaxial. In another example, the first and second accommodating portions may open to different sides of the cap. In a further example, the cap may include at least one seal configured to accommodate an endoscopic instrument therethrough. In yet another example, the at least one seal may be configured to receive the endoscopic instrument from either end of the at least one seal. In a yet further example, the at least one seal may be configured to substantially prevent fluid communication therethrough. In still another example, the at least one seal may normally be closed. In a still further example, the at least one seal may be configured to conform to an outer geometry of the endoscopic instrument extending therethrough. In another example, the at least one seal may include a slit. In a further example, the at least one seal may include two seals each configured to accommodate the endoscopic instrument therethrough. In yet another example, each of the at least two seals may be configured to receive the endoscopic instrument from either end of the seal. In a yet further example, the first accommodating portion may have a substantially annular shape. In still another example, the first accommodating portion may have a substantially circular shape. In a still further example, the cap may include a curved portion configured to be gripped. In another example, the first accommodating portion may have a guide portion. In a further example, the guide portion may include a tapered portion. In yet another example, the first accommodating portion may be configured to not receive the interface of the second endoscope.

According to another aspect of the invention, an embodiment of the invention includes an endoscope channel cap including a main body defining a first space and a second space. Each of the first and second spaces are disposed inwardly from an end of the main body, and the main body includes a first flange at least partially defining the first space to aid in retaining an interface of a first endoscope and a second flange at least partially defining the second space to aid in retaining an interface of a second endoscope.

In various embodiments, the cap may include any combination of various aspects. For example, the main body may define a third space disposed inwardly from the end of the main body, and the main body may include a third flange at least partially defining the third space to aid in retaining an interface of a third endoscope. In another example, the first flange may be configured to retain the interface of the first endoscope received from a first side of the main body, and the second flange may be configured to retain the interface of the second endoscope received from a second side of the main body. In a further example, the first flange may be configured to retain the interface of the first endoscope received from a side of the main body, and the second flange may be configured to retain the interface of the second endoscope received from the side of the main body.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate embodiments of the invention and together with the description, serve to explain the principles of the invention.

FIG. 5 is a side view of a cap interface portion of an endoscope for use with the endoscope channel cap of FIG. 1, shown in cross-section, according to an embodiment of the present invention.

DESCRIPTION OF THE EMBODIMENTS

Figure 1:
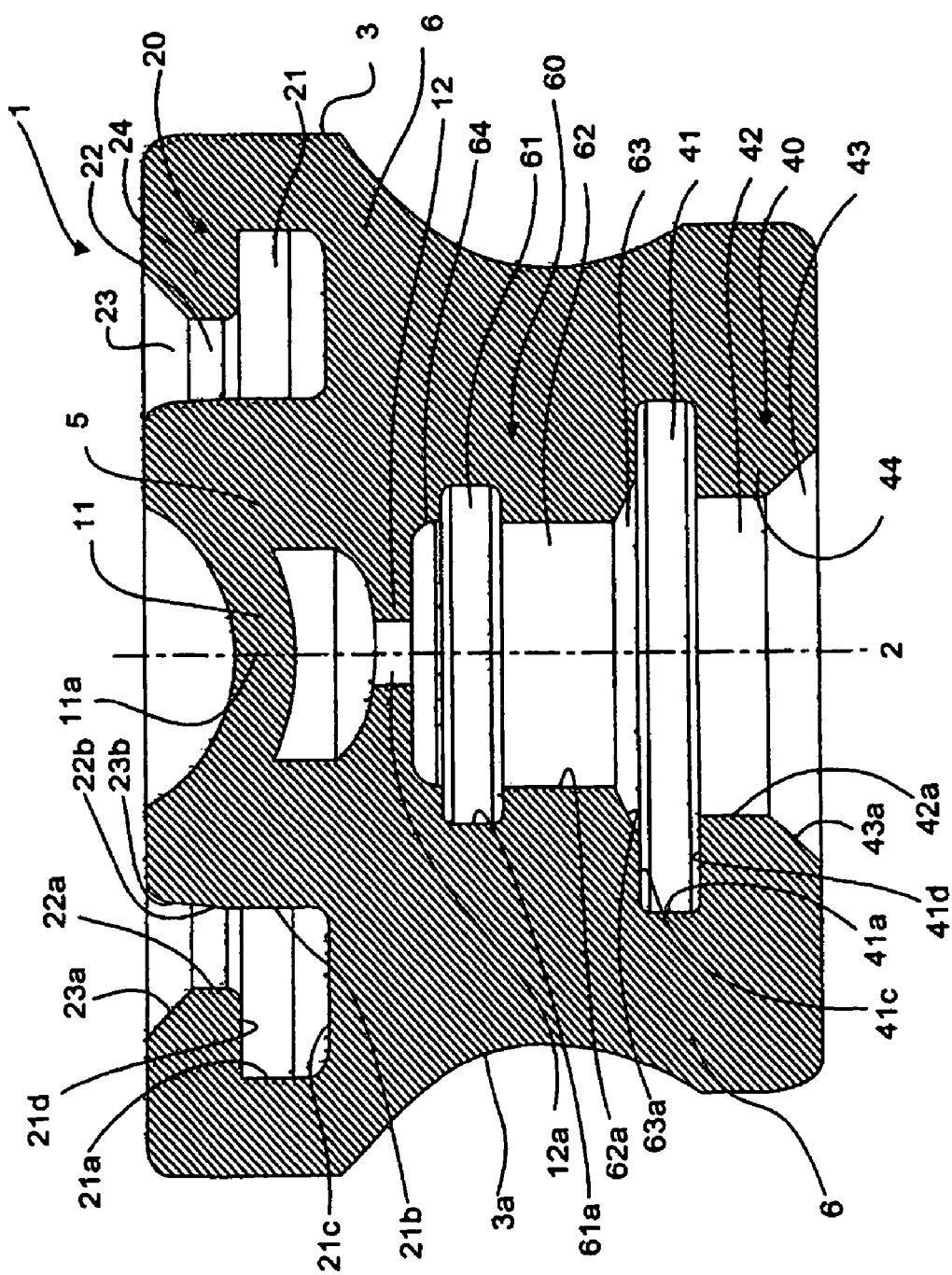
FIG. 1 is a cross-sectional view of an endoscope channel cap according to an exemplary embodiment of the present invention.

Reference will now be made in detail to the present exemplary embodiments of the invention, examples of which are illustrated in the accompanying drawings. Wherever possible, the same reference numbers will be used throughout the drawings to refer to the same or like parts.

Embodiments of the present invention relate to an endoscope channel cap that may be used separately with two or more endoscopes each having a cap interface portion with a different configuration, such as different dimension, shape, or geometry. The channel cap may include two or more accommodating portions/spaces that each receive and retain a cap interface portion of an endoscope. The cap interface portions of the endoscopes have different configurations, each configuration corresponding to an accommodating space of the channel cap. The channel cap also may include one or more seals. In an embodiment, the cap may include a first primary seal and a second secondary seal. The primary seal may assure maintenance of insufflation pressure when an endoscopic instrument is not inserted in the working channel of the endoscope. The secondary seal may be of a material and a configuration to conform to the outside geometry of an endoscopic instrument inserted in the channel cap and endoscope working channel.

FIGS. 1-5 depict an exemplary embodiment of an endoscope channel cap. The endoscope channel cap 1 may have a main body 6 including a first endoscope cap interface accommodating space 20, a second endoscope cap interface accommodating space 40, and a third endoscope cap interface accommodating space 60. The endoscope cap 1 may also include a primary seal 11 and a secondary seal 12.

The various portions of endoscope channel cap 1, and spaces defined by those portions, may have any desired size, shape, dimension, and configuration suitable to receive and retain an interface portion of a corresponding endoscope. The sizes, dimensions, shapes, and configurations described herein are exemplary only and are not meant to limit the scope of the invention.

The first accommodating space 20 may be configured to accommodate a cap interface of a first endoscope. For example, space 20 may accommodate an endoscope 4 having a flanged cap interface 4a, as shown in FIG. 5. As a further example, space 20 may be configured to accommodate a cap interface from an endoscope currently manufactured by FUJI.

The first accommodating space 20 may have a first space 21, a second space 22, and a third space 23. The first space 21 may be configured to accommodate a first portion of the cap interface, for example, a wide proximal-most portion of the cap interface. The second space 22 may be in flow communication with the first space 21, and may be configured to accommodate a second portion of the cap interface, for example, a narrower portion of the cap interface connected to the wide portion of the cap interface. The third space 23 may be in flow communication with the first space 21 and second space 22, and may be configured to assist in the placement of the wide and narrower portions of the cap interface in their respective spaces 21, 22. Spaces 21, 22, and 23 that comprise first accommodating space 20 each have an annular shape and surround a central portion 5 having a longitudinal axis 2. A portion 24 of the main body 6 that defines the second space 22 may have a flange-like configuration. The flange-like portion 24 may interact with a flanged cap interface 4a to retain the cap interface 4 within the space 20.

First space 21 may have a circular shaped outer surface 21a having a diameter of about 0.64 inches and centered on longitudinal axis 2 of the cap 1. Surface 21a may have a thickness of about 0.07 inches. A bottom edge of the outer surface 21a may be curved, with a radius of about 0.3 inches. An inner surface 21b of the first space 21 also may be circular shaped, with a diameter of about 0.395 inches, and centered on longitudinal axis 2 of the cap 1. Surface 21b may be angled at about 5 degrees with respect to the longitudinal axis 2 of the endoscopic cap 1. A bottom surface 21c may connect the outer surface 21a to the inner surface 21b, while a top surface 21d may extend radially inward from the outer surface 21a about 0.07 inches. An inner edge of surface 21d may be chamfered away from the first space 21. Accordingly, the first space, 21 may be configured to accommodate a portion of a cap interface having substantially the same, or possibly slightly smaller, dimensions and configuration.

Second space 22 may have an axial thickness of about 0.23 inches. Second space 22 may have a circular shaped outer surface 22a having a diameter of about 0.5 inches and centered on the longitudinal axis 2 of the cap 1. A portion of the outer surface 22a may be chamfered away from the longitudinal axis 2 of the endoscopic cap 1 such that the outer surface 22a smoothly transitions to a portion of the first space 21, for example the top surface 21d of the first space 21. An inner surface 22b of the second space 22 may also be circular shaped, with a diameter of about 0.395 inches, centered on the longitudinal axis 2, and angled at about 5 degrees with respect to the longitudinal axis 2. Accordingly, the second space 22 may be configured to accommodate a portion of a cap interface having substantially the same, or possibly slightly smaller, dimensions and configuration.

Third space 23 may have a thickness of about 0.57 inches. An outer surface 23a of the third space 23 may be circular shaped, centered on the longitudinal axis 2 of the cap 1, and have a diameter that tapers from about 0.5 inches at the edge where outer surface 23a meets outer surface 22a, to about 0.58 inches at the edge where outer surface 23a meets outer surface 3 of the cap 1. The outer surface 23a may be tapered at an angle of about 45 degrees with respect to the longitudinal axis 2 of the cap 1, outer surface 3, and the outer surface 22a. An inner surface 23b of the third space 23 is a continuation of surface 22b and therefore may be circular shaped, with a diameter of about 0.395 inches, centered on longitudinal axis 2 of the cap 1, and angled at about 5 degrees with respect to the longitudinal axis 2. A portion of the inner surface 23b may be chamfered toward the longitudinal axis 2 of the endoscopic cap 1. Accordingly, the third space 23 may be configured to assist in the placement of the cap interface into the first space 21 and the second space 22 via the third space 23, for example, by directing and guiding the cap interface via the tapered outer surface 23a. Inner surfaces 21b, 22b, 23b may be tapered as described so as to permit easier insertion of the cap interface of the corresponding endoscope.

The second accommodating space 40 may be configured to accommodate a cap interface of another endoscope different than the endoscope that interfaces with space 20. For example, the second accommodating space 40 may be configured to accommodate a cap interface from an endoscope currently manufactured by OLYMPUS. The second space 40 may open to, or be defined by, a different and opposite side of the cap from space 20.

The second accommodating space 40 may have a first space 41, a second space 42, and a third space 43. The first space 41 may be configured to accommodate a first portion of the cap interface, for example, a wide proximal-most portion of the cap interface. The second space 42 may be in flow communication with the first space 41, and may be configured to accommodate a second portion of the cap interface, for example, a narrower portion of the cap interface connected to the wide portion of the cap interface. The third space 43 may be in flow communication with the first space 41 and second space 42, and may be configured to assist in the placement of the wide and narrower portions of the cap interface in their respective spaces 41, 42. A portion 44 of the main body 6 that defines the second space 42 may have a flange-like configuration. The flange-like portion 44 may interact with a flanged cap interface of a corresponding endoscope to retain the cap interface within the space 40.

Second accommodating space 40 may have a first space 41 having an outer surface 41a that is circular shaped. The outer surface 41a may have a diameter of about 0.385 inches, may be centered on the longitudinal axis 2 of the cap 1, and may have a thickness of about 0.05 inches. At least one portion of the outer surface 41a may be curved. A top surface 41c of the first space 41 may extend radially inward from the outer surface 41a about 0.065 inches, while a bottom surface 41d may extend radially inward from the outer surface 41a about 0.0725 inches. Accordingly, the first space 41 may be configured to accommodate a portion of a cap interface having substantially the same, or possibly slightly smaller, outer dimensions and configuration.

Second accommodating space 40 may have a second space 42 having a thickness of about 0.047 inches. An outer surface 42a of the second space 42 may be circular shaped, having a diameter of about 0.24 inches, and may be centered on the longitudinal axis 2 of the cap 1. The outer surface 42a may meet a portion of the first space 41, for example the bottom surface 41d of the first space 41. Accordingly, the second space 42 may be configured to accommodate a portion of a cap interface having substantially the same, or possibly slightly smaller, outer dimensions and configuration.

Second accommodating space 40 may have a third space 43 having a thickness of about 0.053 inches. An outer surface 43a of the third space 43 may have a diameter that tapers from about 0.24 inches at the edge where outer surface 43a meets outer surface 42a, to about 0.32 inches at the edge where outer surface 43a meets outer surface 3 of the cap 1. The outer surface 43a may be circular shaped and may be centered on the longitudinal axis 2 of the cap 1. The outer surface 43a may be tapered at an angle of about 45 degrees with respect to the longitudinal axis 2 of the cap 1 and the outer surface 42a. Accordingly, the third space 43 may be configured to assist in the placement of the cap interface into the first space 41 and the second space 42 via the third space 43, for example, by directing and guiding the cap interface via the tapered outer surface 43a.

The third accommodating space 60 may be configured to accommodate a cap interface of yet another endoscope different than the endoscopes that interface with the first or second accommodating spaces 20, 40. For example, the third accommodating space 60 may be configured to accommodate a cap interface from an endoscope currently manufactured by PENTAX. The third space 60 may open to, or be defined by, a different and opposite side of the cap from space 20. The third space 60 may open to, or be defined by, the same side of the cap 1 as space 40, be coaxial with second space 40, and extend from second space 40.

Figure 2:
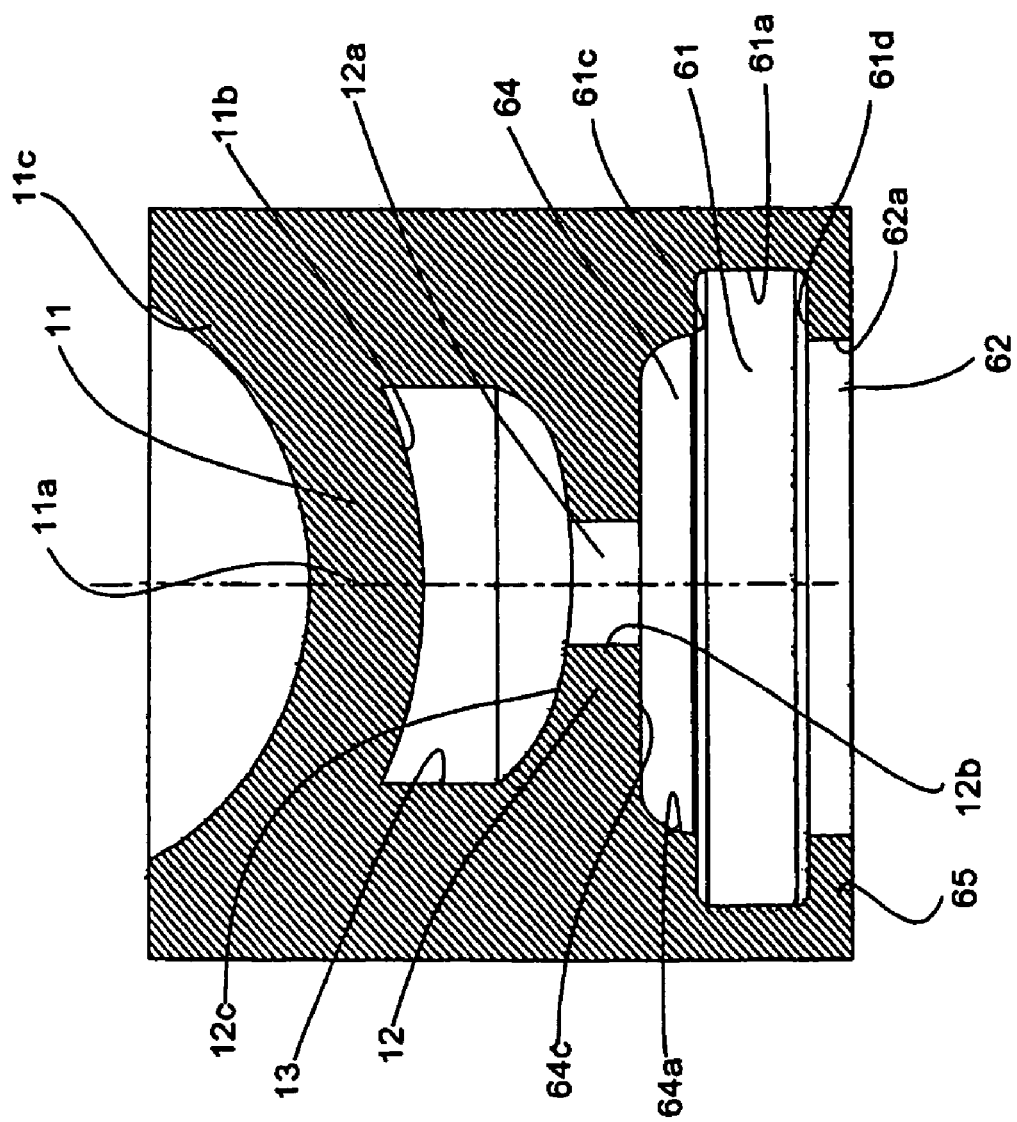
FIG. 2 is a cross-sectional view of a breakaway portion of the endoscope channel cap of FIG. 1.
Figure 3:
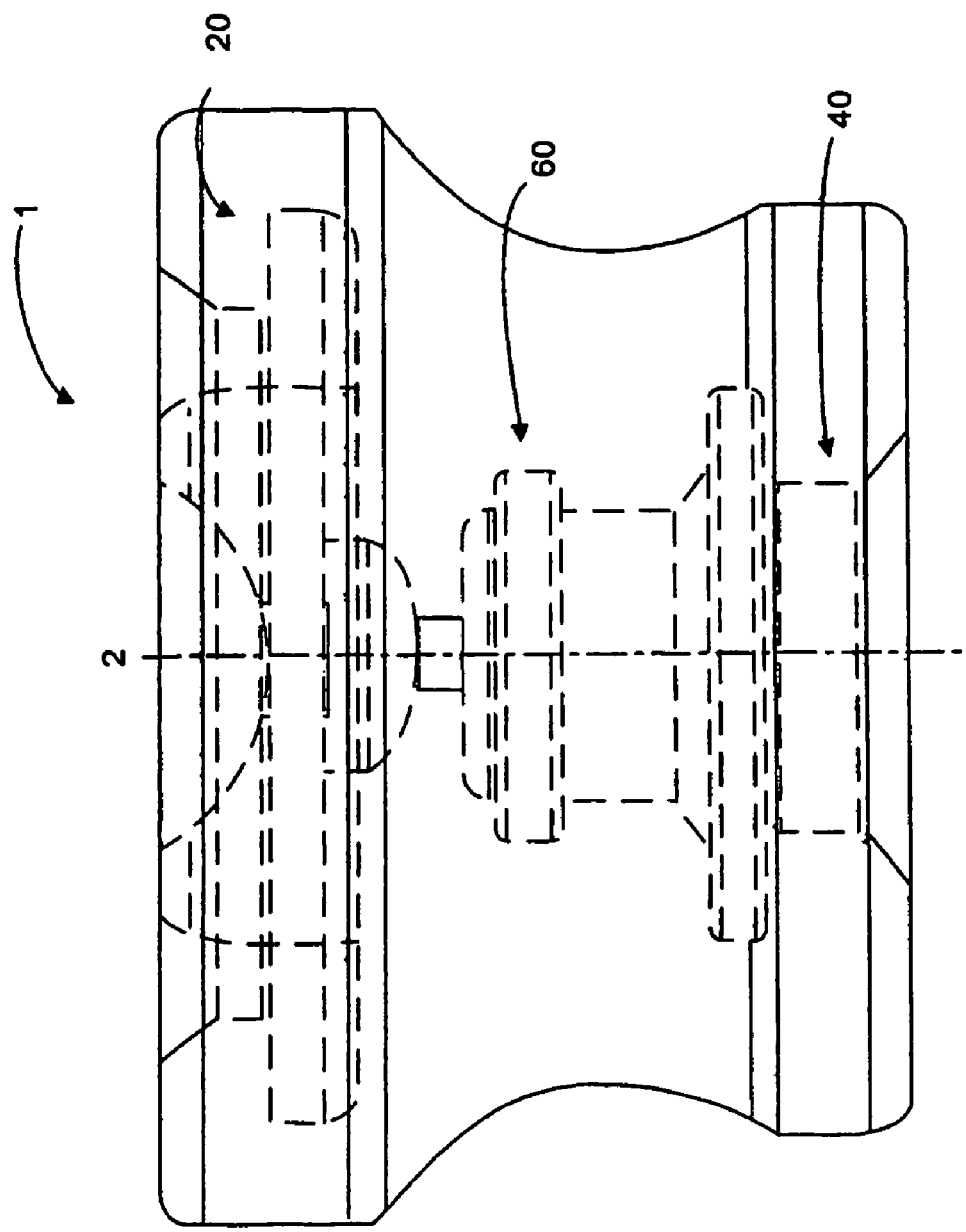
FIG. 3 is a side view of the endoscope channel cap of FIG. 1, showing internal portions in dashed lines.

Third accommodating space 60, shown in FIGS. 1 and 2, may have a first space 61, a second space 62, and a third space 63. The first space 61 may be configured to accommodate a first portion of the cap interface, for example, a wider proximal-most portion of the cap interface. The second space 62 may be in flow communication with the first space 61, and may be configured to accommodate a second portion of the cap interface, for example, a narrower portion of the cap interface connected to the wide portion of the cap interface. The third space 63 may be in flow communication with the first space 61 and second space 62, and may be configured to assist in the placement of the wide and narrower portions of the cap interface in their respective spaces 61, 62. As shown in FIG. 2, a portion 65 of the main body 6 that defines the second space 62 may have a flange-like configuration. The flange-like portion 64 may interact with a flanged cap interface of a corresponding endoscope to retain the cap interface within the space 60.

Third accommodating space 60 may have a first space 61 having an outer surface 61a that may have a circular shape, a diameter of about 0.260 inches, be centered on the longitudinal axis 2 of the cap 1, and have a thickness of about 0.05 inches. At least one portion of the outer surface 61a may be curved. A first top 61c of the first space 61 may extend radially inward from the outer surface 61a about 0.03 inches, while a bottom surface 61d may also extend radially inward from the outer surface 61a about 0.03 inches. Accordingly, the first space 61 may be configured to accommodate a portion of a cap interface having substantially the same, or possibly slightly smaller, outer dimensions and configuration.

Third accommodating space 60 may have a second space 62 having a thickness of about 0.092 inches and a circular shape. An outer surface 62a of the second space 62 may have a diameter of about 0.2 inches and may be centered on the longitudinal axis 2 of the cap 1. The outer surface 62a may meet a portion of the first space 61, for example the bottom surface 61d of the first space 61. Accordingly, the second space 62 may be configured to accommodate a portion of a cap interface having substantially the same, or possibly slightly smaller, outer dimensions and configuration.

Third accommodating space 60 may have a third space 63 having a thickness of about 0.028 inches and a circular shape. An outer surface 63a of the third space 63 may be centered on the longitudinal axis 2 of the cap 1, and may have a diameter that tapers from about 0.2 inches where outer surface 63a meets outer surface 62a, to about 0.255 inches where the outer surface 63a meets an edge of surface 41c. The outer surface 63a may be tapered at an angle of about 45 degrees with respect to the longitudinal axis 2 of the cap 1 and surface 62a. Accordingly, the third space 63 may be configured to assist in the placement of the cap interface into the first space 61 and the second space 62 via the third space 63, for example, by directing and guiding the cap interface via the tapered outer surface 63a.

Main body 6 of cap 1 may define a space 64 having an outer surface 64a with a maximum diameter of about 0.2 inches, centered on the longitudinal axis 2 of the cap, and having a thickness of about 0.025 inches. At least one portion of the outer surface 64a may be curved. For example, the curved portion of the outer surface 64a may have a radius of about 0.02 inches that transitions into a side surface 64c. Top surface 64c may extend radially inward from the outer surface 64a such that an inner portion of the side surface 64c is disposed about 0.025 inches from the longitudinal axis 2 of the cap 1. The fourth space 64 is configured to provide relief and flexibility to the secondary seal 12.

Cap 1 may be made of any suitable biocompatible material known in the art with sufficient strength and tear resistance to fit on an end of an endoscope channel and maintain insufflation pressure. Suitable materials include silicones, rubber, plastic, composites, etc. In various embodiments, at least the portions of the cap 1 defining second spaces 22, 42, 62, and third spaces 23, 43, 63 are comprised of flexible material to allow portions of a cap interface that are wider than these portions of the cap 1 to traverse through at least some of the second spaces 22, 42, 62 and third spaces 23, 43, 63 on their way to one of the first spaces 21, 41, 61. Furthermore, since the second accommodating space 40 leads to the third accommodating space 60, portions defining the second accommodating space 40 may also be made of a sufficiently flexible material to allow portions of a cap interface to enter the third accommodating space 60 via the second accommodating space 40. The endoscope channel cap 1 may have different portions made of different materials, and may be made using any method known in the art, for example, injection molding, machining, vacuum forming, stamping, etc.

Figure 4:
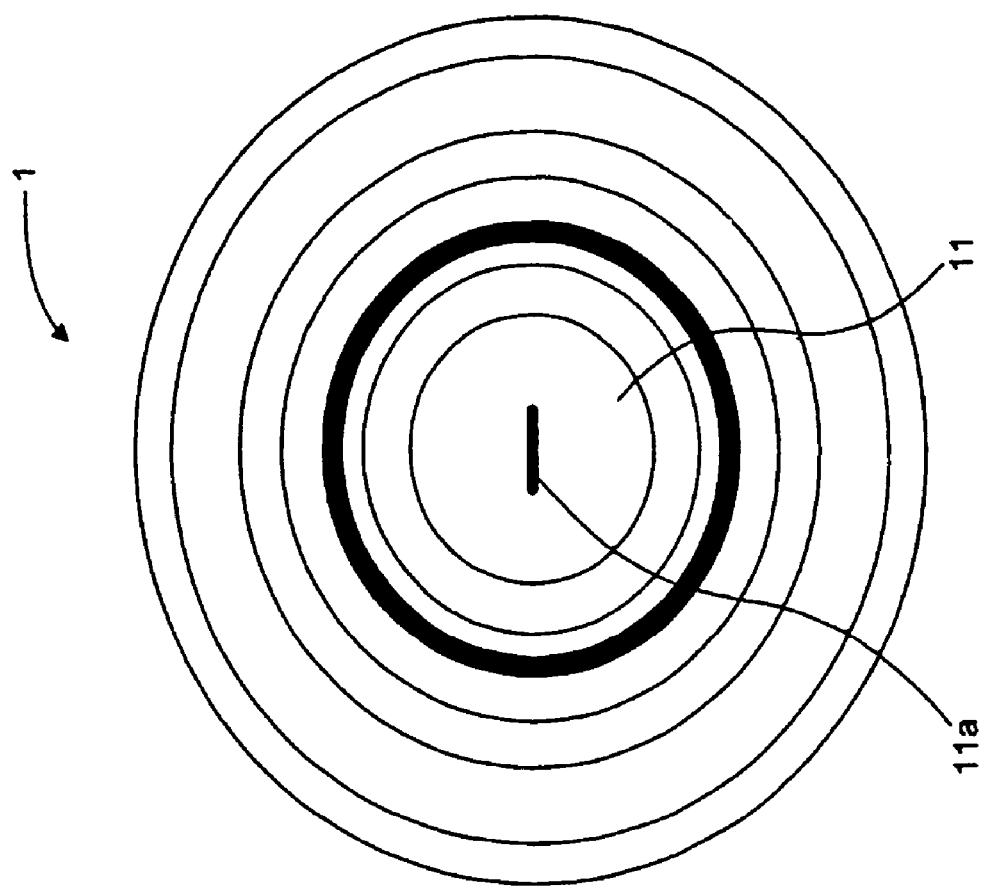
FIG. 4 is an end view of the endoscope channel cap of FIG. 1.

The endoscope channel cap 1 may include a primary seal 11, as shown most clearly in FIGS. 1, 2, and 4. The primary seal 11 may be positioned radially inward from the inner surfaces 21a, 22a, 23a of the first accommodating space 20.

The primary seal 11 is configured to substantially prevent flow communication across the primary seal 11 whether or not an object, such as a catheter of an endoscopic instrument, is disposed therethrough. The material used in the primary seal 11 may differ from the rest of the cap 1. Such a cap 1 may be manufactured using a two-shot molding process.

The primary seal 11 may have a slit 11a configured to accommodate an elongated member of an endoscopic instrument therethrough. As the elongated member enters therethrough, the slit 11a opens. The primary seal 11 and slit 11a may have bidirectional capability in that the elongated member of the endoscopic instrument may be introduced into and advanced through the primary seal 11 and the slit 11a in either direction. The primary seal 11 and slit 11a are normally closed.

As shown in FIG. 1, the primary seal 11 may be inwardly offset from an end of the cap 1 and have a substantially hemispherical configuration. An inner surface 11b of the primary seal 11 may have a radius of about 0.2 inches and an outer surface 11c of the primary seal may have radius of about 0.15 inches. The slit 11a may have a length of about 0.075 inches and a width of about 0.005 inches, and may extend about 0.05 inches between surfaces 11c and 11b. However, the dimensions of the primary seal 11 and its various aspects (e.g., thickness, curvature, spacing, etc.) are exemplary only, and may also be adjusted during manufacture of the cap 1, for example, depending on the characteristics of the endoscopic instrument proposed to be advanced therethrough. For example, the primary seal 11 may have a flat, conical, or duckbill shaped configuration. In other examples, the slit 11a may instead be a star-shaped, cross-shaped, or T-shaped in configuration.

The endoscope channel cap 1 may include a secondary seal 12, as shown most clearly in FIGS. 1 and 2. The secondary seal 12 may include a space 12a positioned radially inward from the portions of the cap 1 that define the secondary seal 12. The space 12a may be configured to have a diameter about the same size as an elongated member of an endoscopic instrument that may be placed through the cap 1. Thus, an inner surface 12b of the secondary seal 12 seals against an outer surface of the elongated member to substantially prevent fluid from traversing the space 12a of the secondary seal 12. The space 12a may be in flow communication with the slit 11a, the third accommodating space 60, and the second accommodating space 40. The secondary seal 12 and space 12a may have bidirectional capability in that the elongated member of the endoscopic instrument may be introduced into and advanced through the secondary seal 12 and the space 12a in either direction. The material used in the secondary seal 12 may differ from the rest of the cap 1. Such a cap 1 may be manufactured using a two-shot molding process.

As shown in FIG. 2, a side surface 12c of the secondary seal 12 may be curved with a radius of about 0.064 inches. Both the space 12a and inner surface 12b may have a diameter of about 0.05 inches, a thickness of about 0.03 inches, and may be centered on the longitudinal axis 2. An intervening surface 13 between the inner surface 11b and side surface 12c may have a thickness of about 0.05 inches, a diameter of about 0.16 inches, and may be centered on the longitudinal axis 2. However, the dimensions of the secondary seal 12 and its various components (e.g., thickness, curvature, spacing, etc.) are exemplary only, and may also be adjusted, for example, depending on the characteristics of the endoscopic instrument being advanced therethrough. For example, the secondary seal 12 and the secondary space 12a may have a non-circular configuration that matches the outer geometry of the endoscopic instrument.

The endoscope channel cap 1 may have an ergonomic configuration. For example, a portion 3a of the outer surface 3 of the cap 1 may be curved inward so that a user may more easily grip and manipulate the cap 1. In another example, at least the outer surface 3 of the cap 1 may be made of a user-friendly material such as rubber, plastic, composites, etc.

In other embodiments, the cap may not define accommodating spaces embedded within and coaxial with each other, but may instead define separate, discrete accommodating spaces that are attached side by side. In such a configuration, each of the accommodating spaces would be configured to accommodate different endoscope interface and would each have their own seal(s). The cap may also be a plurality of caps, each defining a separate, discrete accommodating space with its own seal(s), that are connected together. For example, the plurality of caps may be tethered or hinged together. The cap may also define at least one of the accommodating spaces for receiving at least one of the endoscopes, and when a separate portion defining another accommodating space is needed to receive another endoscope, the separate portion defining another accommodating space may be attached to the cap. For example, a living hinge may slide the separation portion defining another accommodating space into place on the cap.

Various dimensions have been set forth above. These dimensions are exemplary only, and do not limit the scope of the invention in any way, shape, or form. The dimensions and configuration of the various portions of the endoscope channel cap 1 may vary as required and desired.

In an exemplary method of using the endoscope channel cap 1, a user may grip the cap 1 by the curved portion 3a of the outer surface 3. The user may then ascertain which endoscope is being used, and thus decide which endoscope accommodating space 20, 40, 60 will be utilized. The user may then place the cap interface of the endoscope into the appropriate accommodating space 20, 40, 60. In the case where the cap interface will be placed in the third accommodating space 60, the cap interface may first be placed through the second accommodating space 40.

Once the cap interface has been appropriately secured in the appropriate accommodating space 20, 40, 60, and the endoscope has been positioned to a desired body portion, the user may advance an endoscopic instrument through the primary seal 11 and the secondary seal 12, down the working channel of the endoscope, and into the desired body portion. Depending on the orientation of the endoscope channel cap 1, the endoscopic instrument may be advanced through the primary seal 11 and the secondary seal 12 in any order.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An endoscope channel cap, comprising:
    a main body defining a first space and a second space, each of the first and second spaces being disposed inwardly from an outer surface of the main body,
    wherein the main body further defines a third space disposed inwardly from the outer surface of the main body, and wherein the main body includes a third flange projecting radially outward and at least partially defining the third space to aid in retaining an interface of a third endoscope,
    wherein the main body includes a first interior flange at least partially defining the first space to aid in retaining an interface of a first endoscope and a second interior flange at least partially defining the second space to aid in retaining an interface of a second endoscope,
    wherein both the first interior flange and the second interior flange project radially outward toward the main body;
    wherein the first and second spaces open to a first side of the main body;
    a primary seal configured to accommodate an endoscopic instrument therethrough, the primary seal having a slit formed therein; and
    a secondary seal longitudinally spaced from the primary seal, the secondary seal having an inner surface that defines a bidirectional opening extending longitudinally through the secondary seal that is in fluid communication with the primary seal, the bidirectional opening being sized to accommodate the endoscopic instrument extending through the secondary seal and seal against the endoscopic instrument along the opening.

2. The endoscope channel cap of claim 1, wherein the third space opens to a second side of the main body different from the first side.

3. The endoscope channel cap of claim 1, wherein the first interior flange is configured to retain the interface of the first endoscope received from the first side of the main body and the second interior flange is configured to retain the interface of the second endoscope received from the first side of the main body.

4. The endoscope channel cap of claim 1, wherein the third interior flange is configured to retain the interface of the third endoscope received from the second side of the main body.

5. The endoscope channel cap of claim 1, wherein the primary seal and the secondary seal are positioned between the first and second spaces and a second side of the endoscope channel cap.

6. The endoscope channel cap of claim 1, wherein the first interior flange is not configured to retain the interface of the second endoscope.

7. The endoscope channel cap of claim 1, wherein the first interior flange is configured to not retain the interface of either the second or third endoscopes, the second interior flange is configured to not retain the interface of the third endoscope, and the third interior flange is configured to not retain the interface of either the first or second endoscopes.

8. The endoscope channel cap of claim 1, wherein the first and second spaces are fixedly and coaxially disposed relative to each other.

* * * * *

UNITED STATES PATENT AND TRADEMARK OFFICE
CERTIFICATE OF CORRECTION

| | | |
|---|---|---|
| PATENT NO. | : 8,231,525 B2 | Page 1 of 1 |
| APPLICATION NO. | : 11/320491 | |
| DATED | : July 31, 2012 | |
| INVENTOR(S) | : Adam L. Cohen, John Golden and Liem T. Vu | |

It is certified that error appears in the above-identified patent and that said Letters Patent is hereby corrected as shown below:

Column 1
Line 40: delete "insulation" and insert therefor --insufflation--.

Signed and Sealed this
First Day of January, 2013

David J. Kappos
*Director of the United States Patent and Trademark Office*